United States Patent
Oishi (10) Patent No.: US 10,663,436 B2
(45) Date of Patent: May 26, 2020

(54) ACOUSTIC-WAVE ACQUISITION APPARATUS

(71) Applicant: CANON KABUSHIKI KAISHA, Tokyo (JP)

(72) Inventor: Takuji Oishi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/684,798

(22) Filed: Aug. 23, 2017

(65) Prior Publication Data

US 2017/0350869 A1  Dec. 7, 2017

Related U.S. Application Data (63) Continuation of application No. 13/984,365, filed as application No. PCT/JP2012/000779 on Feb. 6, 2012, now Pat. No. 9,766,211.

(30) Foreign Application Priority Data

Feb. 10, 2011 (JP) .................................. 2011-027542
Dec. 20, 2011 (JP) .................................. 2011-278895

(51) Int. Cl.
*G01N 29/26* (2006.01)
*A61B 8/00* (2006.01)
(Continued)

(52) U.S. Cl.
CPC ........... *G01N 29/26* (2013.01); *A61B 5/0095* (2013.01); *A61B 8/406* (2013.01); *A61B 8/429* (2013.01);
(Continued)

(58) Field of Classification Search
CPC .... G01N 29/26; A61B 5/0095; A61B 8/4209; A61B 8/429; A61B 8/444; A61B 8/5215;
(Continued)

(56) References Cited

U.S. PATENT DOCUMENTS

| 9,766,211 B2 * | 9/2017 | Oishi | A61B 5/0095 |
| 2011/0306865 A1 * | 12/2011 | Thornton | A61B 5/0059 |
| | | | 600/407 |
| 2012/0302866 A1 * | 11/2012 | Fukutani | A61B 5/0095 |
| | | | 600/407 |

FOREIGN PATENT DOCUMENTS

| EP | 2148183 A1 * | 1/2010 | ........... A61B 5/0095 |
| JP | 2009-225904 A | 10/2009 | |
| WO | WO-2010030817 A1 * | 3/2010 | ........... A61B 5/0059 |

OTHER PUBLICATIONS

Fatemi, M., et al., "Ultrasound-Stimulated Vibro-Acoustic Spectography", Science, Apr. 3, 1998, pp. 82-85, vol. 280.

\* cited by examiner

*Primary Examiner* — Lisa M Caputo
*Assistant Examiner* — Rose M Miller
(74) *Attorney, Agent, or Firm* — Canon U.S.A., Inc. I.P. Division (57) ABSTRACT

With a detector in which detection elements are placed in a spherical shape, a uniform resolution area is narrow. An acoustic-wave acquisition apparatus of the present invention is equipped with a detector including a plurality of detection elements that receive acoustic waves from a subject, the receiving surfaces of at least some of the detection elements being at different angles. The apparatus includes a scanning unit configured to move at least one of the subject and the detector to change the relative position of the subject and a highest-resolution area determined depending on the placement of the detection elements.

20 Claims, 11 Drawing Sheets

(51) Int. Cl.
*A61B 8/08* (2006.01)
*A61B 5/00* (2006.01)
*A61B 8/15* (2006.01)

(52) U.S. Cl.
CPC .......... *A61B 8/4209* (2013.01); *A61B 8/4444* (2013.01); *A61B 8/5215* (2013.01); *A61B 8/0825* (2013.01); *A61B 8/15* (2013.01); *A61B 8/4494* (2013.01); *A61B 8/587* (2013.01)

(58) Field of Classification Search
CPC ....... A61B 8/0825; A61B 8/15; A61B 8/4494; A61B 8/587; A61B 8/406
USPC ........................................... 73/643; 600/437
See application file for complete search history.

ACOUSTIC-WAVE ACQUISITION APPARATUS

CROSS-REFERENCE TO RELATED APPLICATIONS

This application is a Continuation of U.S. patent application Ser. No. 13/984,365, filed Aug. 8, 2013 (now U.S. Pat. No. 9,766,211), which is a U.S. national stage application of International Patent Application No. PCT/JP2012/000779, filed Feb. 6, 2012, which claims foreign priority benefit of Japanese Patent Application No. 2011-027542, filed Feb. 10, 2011 and No. 2011-278895, filed Dec. 20, 2011, all of which are hereby incorporated by reference herein in their entirety.

TECHNICAL FIELD

The present invention relates to an acoustic-wave acquisition apparatus.

BACKGROUND ART

General ultrasonic diagnostic apparatuses can acquire information inside a living organism by transmitting ultrasonic waves and receiving the ultrasonic waves reflected inside the living organism. This allows a diseased part, such as cancer, to be detected. Furthermore, imaging of physiological information, that is, functional information, of a living organism attracts attention to improve the detection efficiency. Photoacoustic tomography (PAT) that uses light and ultrasonic waves has been proposed as means for imaging functional information.

The photoacoustic tomography is a technology for imaging internal tissue, which serves as the source of acoustic waves, using the photoacoustic effect in which acoustic waves (typically ultrasonic waves) are generated by applying pulsed light generated from a light source to a subject and absorbing the light that has propagated and diffused in the subject. Changes in the received acoustic waves with time are detected at a plurality of locations, and the acquired signals are mathematically analyzed, that is, reconstructed, and information concerning optical characteristic values of the internal part of the subject is visualized in three dimensions.

The resolution of a three-dimensional image obtained using the photoacoustic tomography depends on the following factors, depending on the placement of acoustic detection elements. If a plurality of acoustic detection elements are placed on a planar surface, a resolution in a direction parallel to the placement planar surface (lateral resolution) depends on both the sizes of the receiving portions of the individual acoustic detection elements and frequencies that the acoustic detection elements can detect, and a resolution in a direction perpendicular to the placement planar surface (depth resolution) depends only on frequencies that the acoustic detection elements can detect. The resolution in the direction perpendicular to the placement planar surface is higher than the resolution in the parallel direction because it is generally easier to increase the frequencies that can be detected by the acoustic detection elements than decrease the size of the receiving portions. In the case where a plurality of acoustic detection elements are placed on a spherical surface, information in the depthwise direction of all of the acoustic detection elements are superimposed, and thus, the lateral resolution is also equal to the depth resolution. That is, since the resolution in all directions depends only to the frequencies, this placement offers high resolution. With intermediate placement between planar placement and spherical placement in which a plurality of acoustic detection elements are placed on a plurality of planar surfaces provided at different angles, the resolution less depends on the sizes of the receiving portions of the acoustic detection elements as the placement approaches from the planar placement to the spherical placement, thus allowing higher resolution to be achieved.

An example of an apparatus in which a plurality of acoustic detection elements are placed on a spherical surface is disclosed in PTL 1. In PTL 1, acoustic detection elements are placed in a spiral pattern on a hemispherical surface, and light irradiation and reception of acoustic waves using the acoustic detection elements are performed while the hemisphere is being rotated about a line connecting the poles of the hemisphere and the center of the sphere. Image reconstruction is performed to obtain image data by using signals output from the acoustic detection elements that have received the acoustic waves.

CITATION LIST

Patent Literature

[PTL 1]
U.S. Pat. No. 5,713,356

SUMMARY OF INVENTION

Technical Problem

However, with the spherical placement of the acoustic detection elements disclosed in PTL 1, the resolution is the highest at the center of the sphere and decreases with a decreasing distance to the periphery, resulting in variations in resolution. In other words, since acoustic waves are incident at right angles on all of the acoustic detection elements at the center, so that signals in the same phase enter at the same time, the signals do not weaken. However, at portions other than the center, acoustic waves are diagonally incident on some of the acoustic detection elements, so that signals in the same phase enter with a time lag. Thus, the weakening of the signals other than those at the center is one of the causes of the variations in resolution.

Another cause is the directivity of the acoustic detection elements. The traveling direction of the acoustic waves is angled with respect to the acoustic detection elements, and the acoustic detection elements have directivity. Thus, the sensitivity is decreased when the traveling direction is angled and is lost when the signal becomes weaker than noise level. Thus, the resolution is decreased as the amount of information decreases. For the planar surface type, when acoustic detection elements are placed on a planar surface that is sufficiently wider than the measuring range, a uniform resolution can be achieved in the measuring range. For intermediate placement between planar placement and spherical placement in which a plurality of planar surfaces are arranged, a uniform-resolution range decreases gradually as the placement shifts from the planar placement to the spherical placement. Thus, high resolution and the uniformity of resolution have a trade-off relationship.

The present invention has been made on the basis of such problem recognition. The present invention reduces variations in resolution depending on the location.

Solution to Problem

An acoustic-wave acquisition apparatus according to an aspect of the present invention is equipped with a detector including a plurality of detection elements that receive acoustic waves from a subject, the receiving surfaces of at least some of the detection elements being at different angles. The apparatus includes a scanning unit configured to move at least one of the subject and the detector to change the relative position of the subject and a highest-resolution area determined depending on the placement of the detection elements.

Advantageous Effects of Invention

The present invention can reduce variations in resolution depending on the location as compared with the related art.

DESCRIPTION OF EMBODIMENTS

The present invention is characterized in that variations in resolution are reduced by moving at least one of a subject and an acoustic array detector in which a plurality of acoustic detection elements are arrayed. Embodiments of the present invention will be described hereinbelow with reference to the drawings.

First Embodiment

A first embodiment is a basic embodiment of the present invention. First, the components of this embodiment will be described, and then a method for placing acoustic detection elements and a method for scanning, which are features of the embodiment of the present invention, will be described. Thereafter, a method of this embodiment will be described, and lastly conceivable variations will be described.

Figure 1:
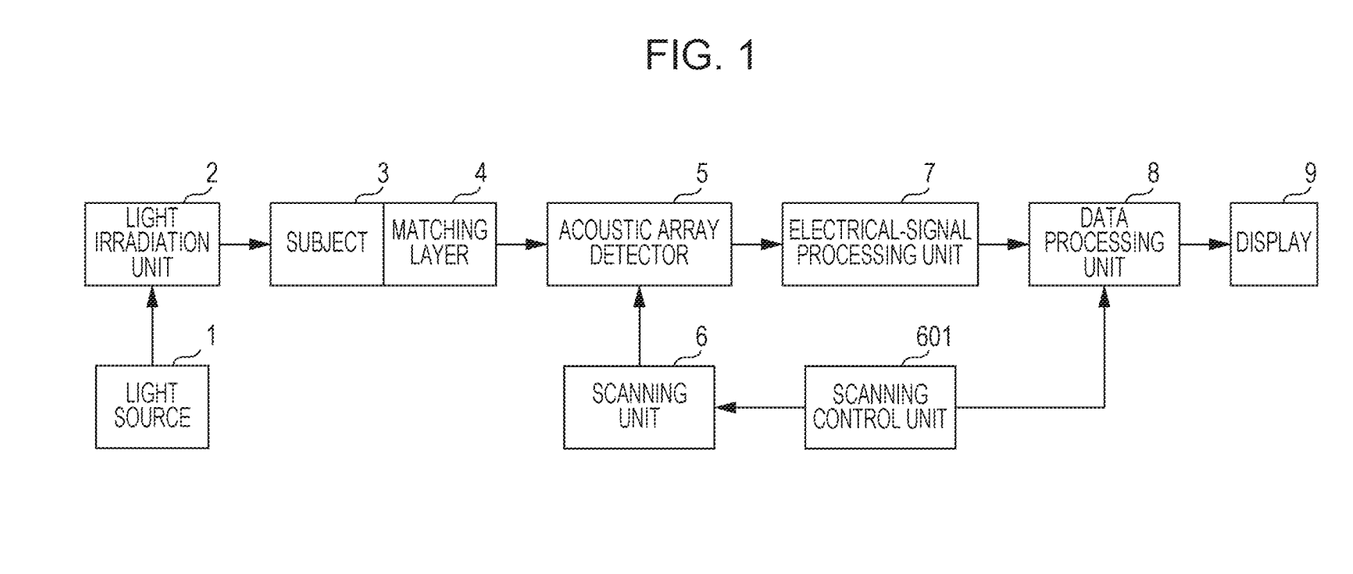
FIG. 1 is a block diagram showing the configuration of an apparatus according to a first embodiment of the present invention.

FIG. 1 is a block diagram showing the components of the first embodiment. An acoustic-wave acquisition apparatus of this embodiment includes a light source 1, a light irradiation unit 2, an acoustic array detector 5, a scanning unit 6, an electrical-signal processing unit 7, a data processing unit 8, and a display 9. The components and a subject will be described hereinbelow.

[Light Source]

The light source 1 is a device that generates pulsed light. To obtain high output, the light source 1 may be a laser or a light-emitting diode. To generate photoacoustic waves effectively, the subject should be irradiated with light for sufficiently short time depending on the thermal properties of the subject. If the subject is a living organism, it is preferable to set the pulse width of pulsed light generated from the light source 1 to tens of nanoseconds or less. Preferably, the wavelength of the pulsed light is in a near-infrared region called a therapeutic window, that is, about 700 nm to 1,200 nm. Light in this region can reach relatively deep in a living organism, thus allowing information of a deep part to be acquired. If measurement is restricted to the surface of a living organism, visible light with a wavelength from about 500 nm to 700 nm and light in the near-infrared region may be used. It is also preferable that the wavelength of the pulsed light have a high absorption coefficient for an observation target.

[Light Irradiation Unit]

The light irradiation unit 2 is a unit that guides pulsed light generated from the light source 1 to a subject 3. Specific examples include optical devices, such as an optical fiber, a lens, a mirror, and a diffuser. The shape and density of the pulsed light are sometimes changed using these optical devices. The optical devices are not limited to the above examples and may be any devices that satisfy the above functions.

[Subject]

The subject 3 is the object to be measured. Specific examples include a living organism, such as a breast, and, for adjustment of an apparatus, phantoms that simulate the acoustic characteristics and optical characteristics of a living organism. Specifically, the acoustic characteristics are a propagation speed and an attenuation rate of acoustic waves, and the optical characteristics are a light absorption coefficient and a light scattering efficient. The subject 3 needs therein a light absorber having a high light absorption coefficient. Examples of the light absorber in a living organism include hemoglobin, water, melanin, collagen, and lipid. For the phantom, a substance that imitates optical characteristics is sealed in as a light absorber. In the present invention, examples of the distribution of information inside the subject 3, generated by receiving acoustic waves, include an initial sound pressure distribution of acoustic waves generated due to light irradiation, a light energy absorption density distribution derived from the initial sound pressure distribution, an absorption coefficient distribution, and a density distribution of substances that constitute the tissue. Examples of the substance density distribution include an oxygen saturation distribution and an oxidation-reduction hemoglobin density distribution.

[Matching Layer]

The matching layer 4 is an impedance matching material that fills a space between the subject 3 and the acoustic array detector 5 to acoustically bond the subject 3 and the acoustic array detector 5. A material thereof can be liquid that has acoustic impedance close to those of the subject 3 and the acoustic detection elements and that allows pulsed light to pass therethrough. Specific examples include water, caster oil, and gel. Since the relative position of the subject 3 and the acoustic array detector 5 changes, as will be described later, both the subject 3 and the acoustic array detector 5 may be placed in a solution that forms the matching layer 4.

[Acoustic Array Detector]

The acoustic array detector 5 is a detector including a plurality of acoustic detection elements that convert acoustic waves into electrical signals. The acoustic array detector 5 is placed on a surface in contact with the solution that forms the matching layer 4 so as to surround the subject 3. The acoustic detection elements that receive acoustic waves from the subject 3 may have high sensitivity and a wide frequency band. Specific examples include acoustic detection elements using PZT, PVDF, cMUT, and a Fabry-perot interferometer. However, the acoustic detection elements are not limited to the above examples and may be any acoustic detection elements that satisfy the above function.

[Scanning Unit]

The scanning unit 6 is a unit that scans (moves) the acoustic array detector 5 in three dimensions. In this embodiment, the subject 3 is fixed, and the acoustic array detector 5 is moved (scanned) using an XYZ stage as the scanning unit 6 to change the relative position of the subject 3 and the acoustic array detector 5. However, in the present invention, the relative position of the subject 3 and the acoustic array detector 5 need only be changed; the acoustic array detector 5 may be fixed, and the subject 3 may be scanned. When the subject 3 is to be moved, a configuration in which the subject 3 is moved by moving a supporting unit (not shown) that supports the subject 3 is conceivable. Alternatively, both the subject 3 and the acoustic array detector 5 may be moved. The scanning may be continuously performed but may be repeated in fixed steps. The scanning unit 6 can be an electrically driven stage equipped with a stepping motor or the like but may also be a manual stage. The scanning unit 6 is not limited to the above examples but may be any scanning unit configured to move at least one of the subject 3 and the acoustic array detector 5.

[Scanning Control Unit]

The scanning control unit 601 controls the scanning unit 6 to move the subject 3 and the acoustic array detector 5 relative to each other. Specifically, the scanning control unit 601 determines the moving speed and direction of the scanning unit 6 and instructs the scanning unit 6 of them. The scanning control unit 601 outputs information on the moving speed and direction of the scanning unit 6 to the data processing unit 8.

[Electrical-Signal Processing Unit]

The electrical-signal processing unit 7 has the function of amplifying analog electrical signals (receiver signals) output from the acoustic array detector 5 and converts the analog signals to digital signals (digital receiver signals). To efficiently obtain data, the electrical-signal processing unit 7 may have the same number of analog-digital converters (ADC) as that of the acoustic detection elements of the acoustic array detector 5; however, one ADC may be connected by turns.

[Data Processing Unit]

The data processing unit 8 generates image data (image reconstruction) by processing the digital signals obtained by the electrical-signal processing unit 7. Specific examples of the data processing unit 8 include a computer and an electrical circuit. Examples of image reconstruction include Fourier transformation, universal back projection, filtered back projection, and iterative reconstruction. The present invention may use any image reconstruction.

[Display]

The display 9 displays image data created by the data processing unit 8 as an image. Specific examples include a liquid crystal display and an organic EL display. The display 9 may be separated from the acoustic-wave acquisition apparatus of the present invention.

Next, a method for placing a plurality of acoustic detection elements 501 and a method for scanning the acoustic array detector 5, which are features of the present invention, will be described. The placement method according to an embodiment of the present invention will be described using FIG. 2. The acoustic detection elements 501 are fixed to a container whose inner wall (subject 2 side) is hemispherical, and the receiving surfaces thereof face the center of the hemisphere. In the case of the placement of FIG. 2, the resolution of an image acquired using universal back projection is highest at the center of the hemisphere and decreases with an increasing distance from the center. Even if the acoustic detection elements 501 are not placed on a spherical surface, the highest-resolution area depends uniquely on the placement of the acoustic detection elements 501.

Figure 2:
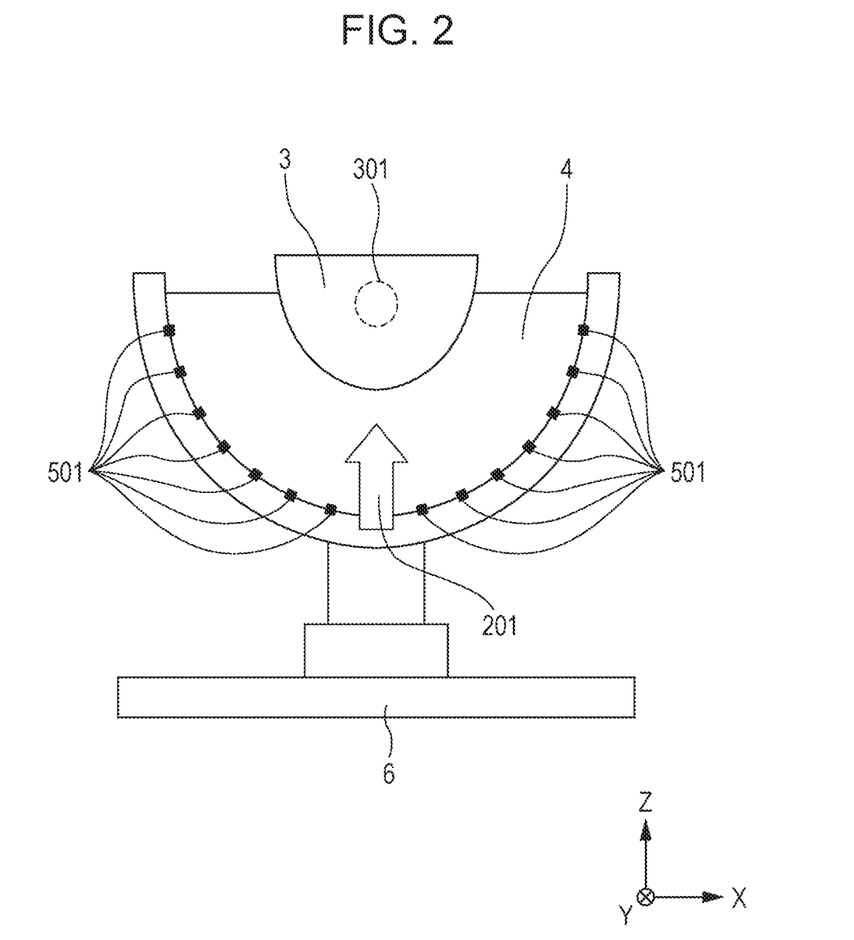
FIG. 2 is a schematic diagram illustrating the apparatus according to the first embodiment of the present invention.

Here, in the present invention, a high-resolution area in the vicinity of the center that is the highest-resolution area is defined as a high-resolution area 301. The range of the high-resolution area 301 depends on how much difference from the highest resolution is permitted. For example, if the acoustic detection elements 501 are placed in a spherical shape, the diameter r of the high-resolution area 301 is expressed by Equation (1).

[Math. 1]

$$r = \frac{r_0}{\varphi_d} \cdot \sqrt{(R^2 - R_H^2)} \qquad (1)$$

where R is an allowable resolution, $R_H$ is the highest resolution, $r_0$ is the diameter of a sphere on which the acoustic detection elements 501 are placed, and $r_d$ is the diameter of each of the acoustic detection elements 501. By changing the relative position of the high-resolution area 301 and the subject 3 and performing reconstruction, the resolution is uniformized. In the present invention, by changing the relative position of the highest-resolution area and the subject 3, the relative position of the high-resolution area and the subject 3 is eventually changed.

In the present invention, the sphere includes not only a perfect sphere but also an ellipsoid expressed by Equation (2) (a shape formed by expanding an ellipse in three dimensions, whose surface is formed of a quadric surface).

[Math. 2]

$$\frac{x^2}{a^2} + \frac{y^2}{b^2} + \frac{z^2}{c^2} = 1 \qquad (2)$$

where a, b, and c are lengths of halves of the diameters in the x-axis, y-axis, and z-axis directions, respectively. An ellipsoid that satisfies a=b=c is a perfect sphere. An ellipsoid in which two of a, b, and c are equal is a spheroid that is obtained by rotating an ellipse around the axis of the ellipse. The sphere in the present invention also includes a spheroid. An ellipsoid is symmetric with respect to an x-y plane, a y-z plane, and a z-x plane, like a sphere.

In measurement, the inside of the hemispherical surface of the acoustic array detector 5 is filled with a solution serving as the matching layer 4, and the subject 3 is placed in the solution. Laser light 201 is emitted so as to irradiate the subject 3 from the lower part (pole) of the hemispherical container. The acoustic array detector 5 is scanned by the XYZ stage, which is the scanning unit 6, so that the position relative to the subject 3 is changed. Thus, the high-resolution area 301 scans across the subject 3. Here, to obtain uniform resolution, the high-resolution area 301 may be scanned in the direction of nonuniform resolution, that is, the direction of gradient of the resolution. The effects thereof will be described later.

Figure 3A:
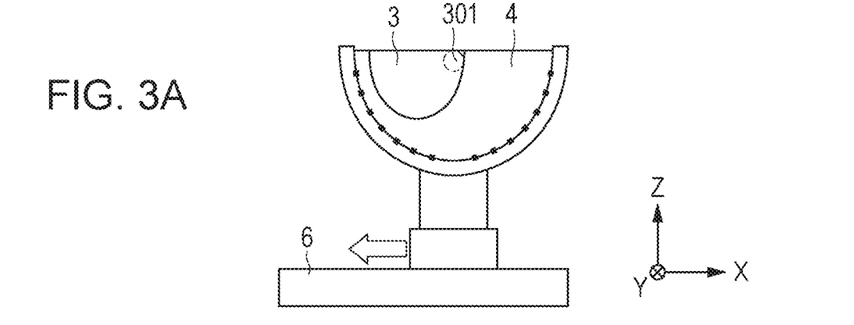
FIG. 3A is a diagram illustrating a scanning method according to the first embodiment of the present invention.
Figure 3B:
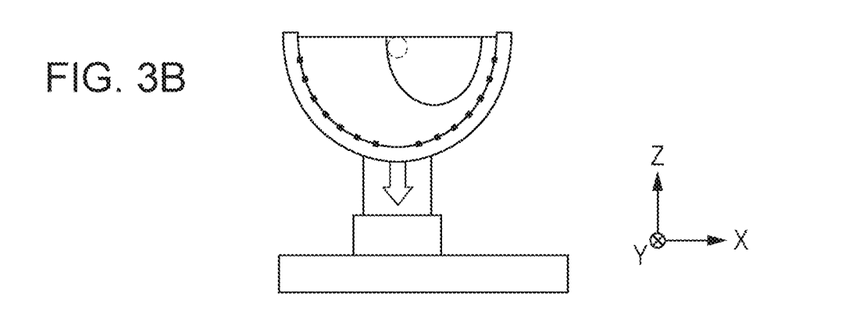
FIG. 3B is a diagram illustrating the scanning method according to the first embodiment of the present invention.
Figure 3C:
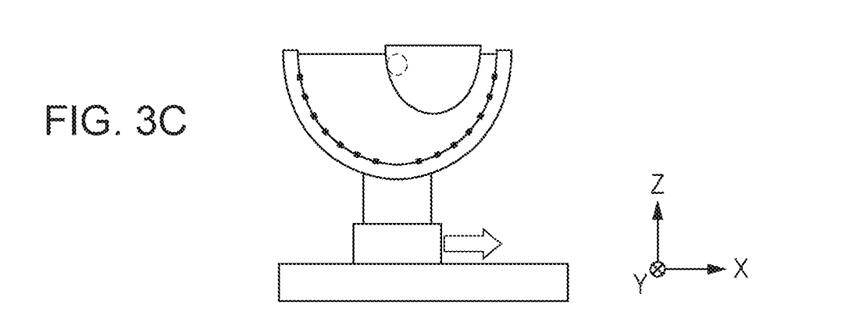
FIG. 3C is a diagram illustrating the scanning method according to the first embodiment of the present invention.
Figure 3D:
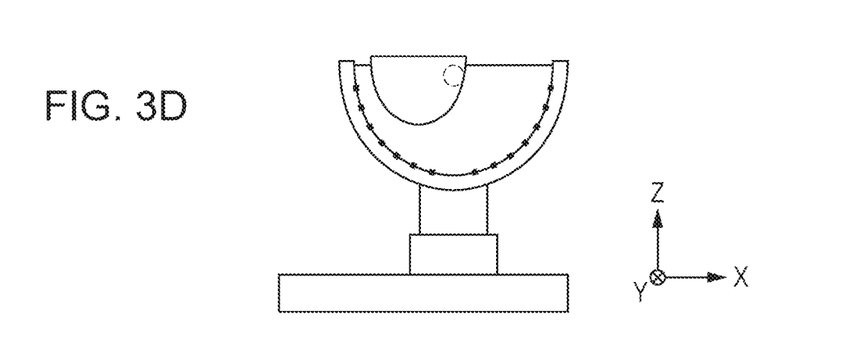
FIG. 3D is a diagram illustrating the scanning method according to the first embodiment of the present invention.

FIGS. 3A to 3D illustrate a specific scanning method. FIG. 3A shows an initial position. Receiver signals are obtained while the entire acoustic array detector 5 is scanned in the direction of the arrow (to the left in the plane of the drawing) using the XYZ stage. When the acoustic array detector 5 has reached the position in FIG. 3B, the entire acoustic array detector 5 is scanned downward in the plane of the drawing to reach the state shown in FIG. 3C. Subsequently, the scanning and signal acquisition are performed until the positional relationship in FIG. 3D is reached. After the operation is performed over the whole one plane (in the X-Z plane), the acoustic array detector 5 is moved in the depthwise direction (Y-direction) in the plane of the drawing, and the scanning and signal acquisition are performed in the same way.

Next, a measuring method of this embodiment will be described with reference to FIG. 4. First, the light irradiation unit 2 irradiates the subject 3 with pulsed light (S1). Acoustic waves excited in a light absorber in the subject 3 by the radiated pulsed light are received by the acoustic detection elements 501 and are converted to receiver signals. The receiver signals are converted to digital signals by the electrical-signal processing unit 7 (S2). At the same time, the data processing unit 8 acquires scanning position information corresponding to the acquired digital signals from the scanning control unit 601 (S3).

Next, the scanning control unit 601 determines whether the high-resolution area 301 has finished scanning an entire measuring area (S4). The entire measuring area is not the entire subject 3 but may be any designated area. If the scanning has not been finished, the acoustic array detector 5 is scanned while the positional relationship among the acoustic detection elements 501 is fixed (S5), and the application of the pulsed light and the acquisition of signals of the acoustic waves are repeated. "Fixing the positional relationship among the acoustic detection elements" means not moving the placement positions of the acoustic detection elements 501 on the acoustic array detector 5.

In S5, the scanning and the acquisition of the receiver signals may be performed at regular intervals. In particular, the acoustic array detector 5 can be moved so that the pulsed light is applied at least one time while the relative position of the high-resolution area 301 and the subject 3 changes by a distance equal to the size (diameter) of the high-resolution area 301. This means that receiver signals are acquired at least one time while the high-resolution area 301 moves a distance equal to the size of the high-resolution area 301.

The smaller the distance scanned during the time from one light irradiation to the next light irradiation, the more the resolution can be uniformized. However, a small scanning distance (that is, a low scanning speed) results in an increase in measurement time. Thus, the scanning speed and the receiver-signal acquisition time interval may be set as appropriate in consideration of desired resolution and measurement time.

The scanning is performed in three dimensions and in the direction of the gradient of the resolution. After the scanning across the entire measuring area is finished, the data processing unit 8 executes image reconstruction based on the obtained digital signals and scanning position information (S6). In the universal back projection used in the image reconstruction, the acquired digital signals are subjected to pre-processing, such as differentiation and noise filtering, and are then subjected to inverse projection in which the signals are propagated from the positions of the acoustic detection elements 501 in the reverse direction. This is performed on the acoustic array detector 5 at all scanning positions, and the propagated processed signals are superimposed. This processing allows a subject-information distribution, such as an absorption coefficient distribution, to be acquired as image data. Finally, the data processing unit 8 outputs the acquired image data to the display 9, and the display 9 displays an image (S7).

Figure 5A:
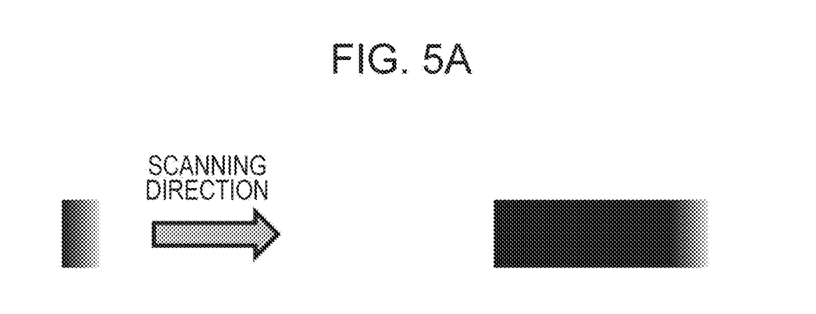
FIG. 5A is a conceptual diagram illustrating the gradient of resolution and the effect of scanning.
Figure 5B:
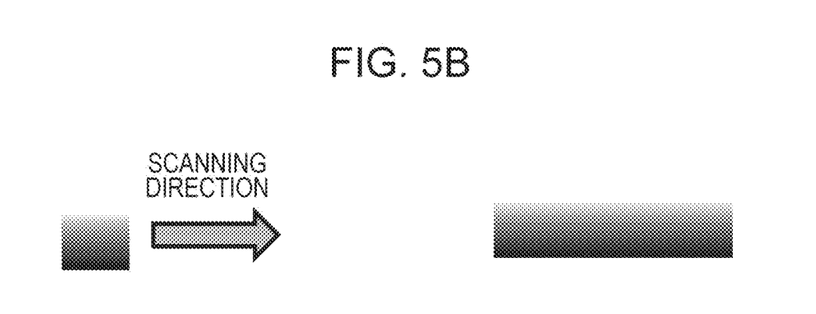
FIG. 5B is a conceptual diagram illustrating the gradient of resolution and the effect of scanning.

FIGS. 5A and 5B are schematic diagrams illustrating the effects of uniformization of resolution in the scanning direction. The tones express resolutions at individual locations, in which a dark tone expresses high resolution, and a light tone expresses low resolution. FIG. 5A shows a resolution with a lateral gradient. If scanning is performed in the direction of the gradient of resolution, the resolution in the lateral direction is uniformized at high resolution except the area at the right end, which is a scanning end portion.

On the other hand, FIG. 5B shows a resolution with a vertical gradient. If scanning is performed in the direction in which no resolution gradient is present, the vertical resolution is not uniformized. In this embodiment, since the acoustic detection elements 501 are placed on a spherical surface, the resolution gradient is present in all directions from the center of the sphere, and thus, scanning may be performed in any directions.

Next, conceivable variations (modifications of the first embodiment) of the present invention will be described. The scanning unit 6 need only perform three-dimensional scanning including not only linear scanning but also rotational scanning. Specifically, the motion of rotating the acoustic array detector 5 about the optical axis of the laser light 201, shown in FIG. 2 and linear scanning may be combined. The scanning may be performed so as to have a short path length.

To uniformize the resolution of the entire subject 3, it is preferable that the hemispherical container serving as the acoustic array detector 5 be twice or larger as the subject 3 so that the high-resolution area 301 can scan the entire subject 3. In other words, in the case where a holding member (a subject holder 10 shown in FIG. 8, described later) for holding the subject 3 is used, it is preferable that the inside diameter of the acoustic array detector 5 (the diameter of the hemispherical surface on which the acoustic detection elements 501 are provided) be twice or larger as the outside diameter of the holding member.

Furthermore, when three-dimensional scanning is performed, the volume of the subject 3 in the solution serving as the matching layer 4 is changed. Therefore, an inlet through which the solution is poured and an outlet through which the solution is discharged may be provided to keep the level of the solution constant, thereby adjusting the amount of the solution.

The acoustic detection elements 501 may be placed in a spherical shape; alternatively, they need not necessarily be placed in the spherical shape but need only be placed on a curved surface or a planar surface to obtain a predetermined highest-resolution area. That is, in the present invention, the acoustic detection elements 501 need only be placed so that the receiving surfaces face the subject 3, and the receiving surfaces of at least some of the acoustic detection elements 501 are at different angles. In other words, some of the acoustic detection elements 501 may be placed in a concave shape with respect to the subject 3 so that the receiving surfaces are at different angles. Of course, the resolution less depends on the size of the receiving portions of the acoustic detection elements 501 as the placement of the acoustic detection elements comes close to a spherical shape.

Figure 6A:
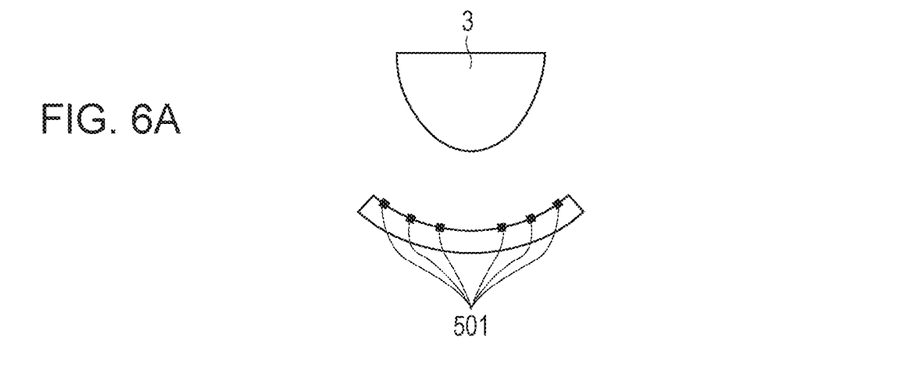
FIG. 6A is a diagram illustrating a modification of the apparatus according to the first embodiment of the present invention.
Figure 6B:
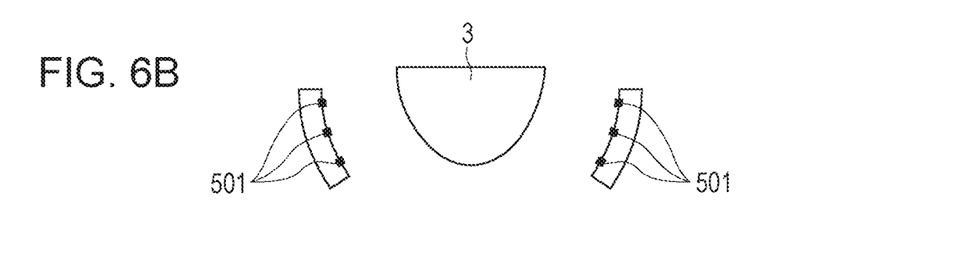
FIG. 6B is a diagram illustrating a modification of the apparatus according to the first embodiment of the present invention.
Figure 6C:
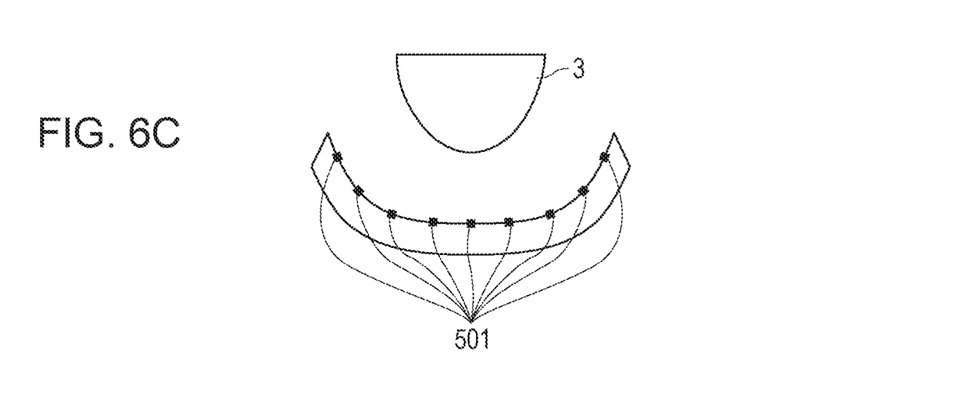
FIG. 6C is a diagram illustrating a modification of the apparatus according to the first embodiment of the present invention.
Figure 6D:
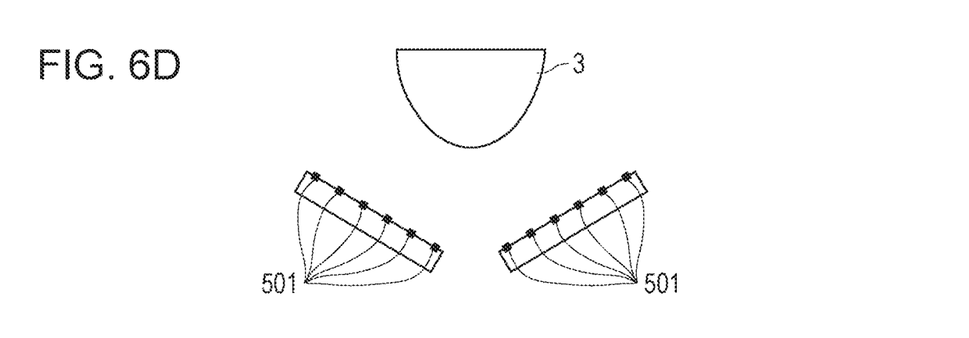
FIG. 6D is a diagram illustrating a modification of the apparatus according to the first embodiment of the present invention.

FIGS. 6A to 6D illustrate examples of the placement of the acoustic detection elements 501 applicable to the present invention. In FIGS. 6A and 6B, the acoustic detection elements 501 are placed along the curved surface of part of the spherical surface. Here, the curved surface in the present invention includes not only a perfectly smooth curved surface but also a curved surface having partial irregularities. The configurations shown in FIGS. 6A and 6B allow flexible placement of the light irradiation unit 2 and so on. In FIG. 6C, the acoustic detection elements 501 are placed along a curved surface that is not spherical. In such a case, the trade-off of the resolution and the uniformity of resolution can be adjusted. In FIG. 6D, the acoustic detection elements 501 are placed in two linear patterns (planar shapes). In such a case, since the acoustic detection elements 501 are placed in linear patterns with two different angles so as to surround the subject 3, a wide uniform resolution area can be provided, and the scanning step width can be increased. Although FIGS. 6B and 6D show examples in which the number of curved surfaces or planar surfaces on which the acoustic detection elements 501 are placed is two, the acoustic detection elements 501 in the present invention may be placed on surfaces more than that or, of course, on one continuous surface. Any desired number of acoustic detection elements 501 may be provided.

In this embodiment, the configuration and processing method described above allows the resolution of an image acquired in the entire measuring area to be higher than or equal to the high resolution and lower than or equal to the highest resolution, and the variations of the resolution to be reduced, that is, a uniform resolution area to be increased.

Second Embodiment

[Signal-Attenuation Correction]

In a second embodiment, a configuration for correcting receiver signals will be described. When acoustic waves propagate in the subject 3 and the matching layer 4, the intensity of the acoustic waves is attenuated. The distance of propagation of the generated acoustic waves in the subject 3 and the distance of propagation in the matching layer 4 in the path from the acoustic-wave generation position to the acoustic detection elements 501 depend on the scanning position of the acoustic array detector 5. In the case where the attenuation rates of the subject 3 and the matching layer 4, which are formed of a living organism and water or the like, respectively, differ, a correct contrast cannot sometimes be calculated. Thus, in this embodiment, a method for correcting different intensity attenuations will be described.

Figure 7:
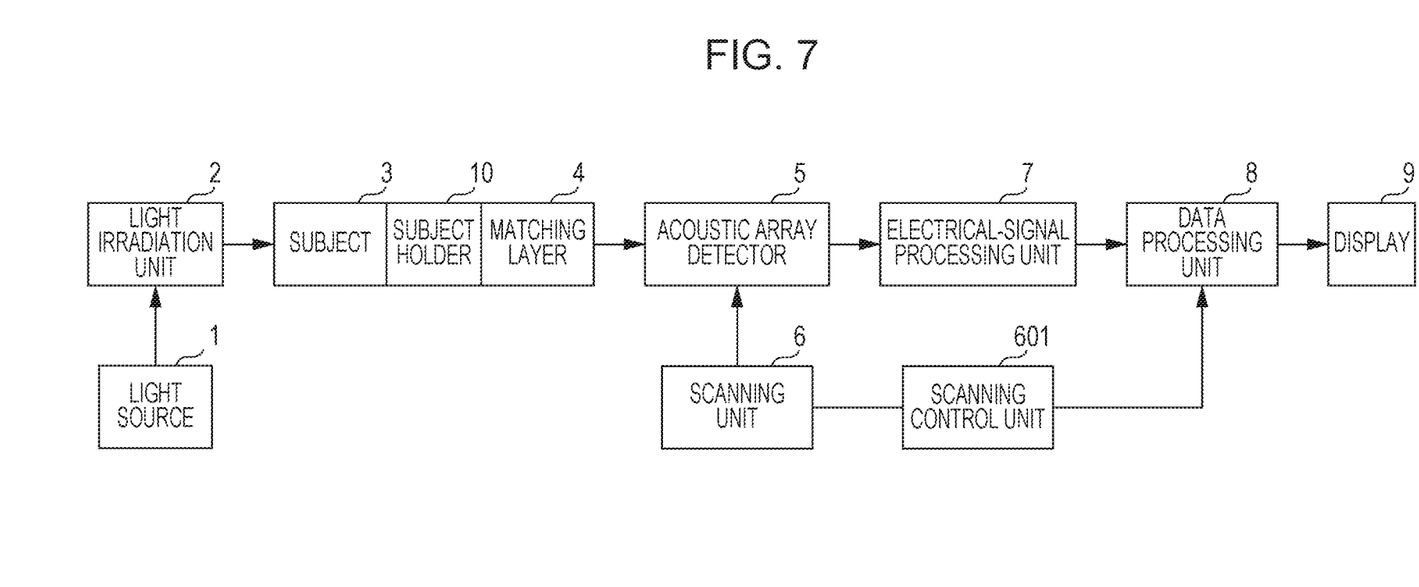
FIG. 7 is a block diagram showing a configuration of an apparatus according to a second embodiment of the present invention.
Figure 8:
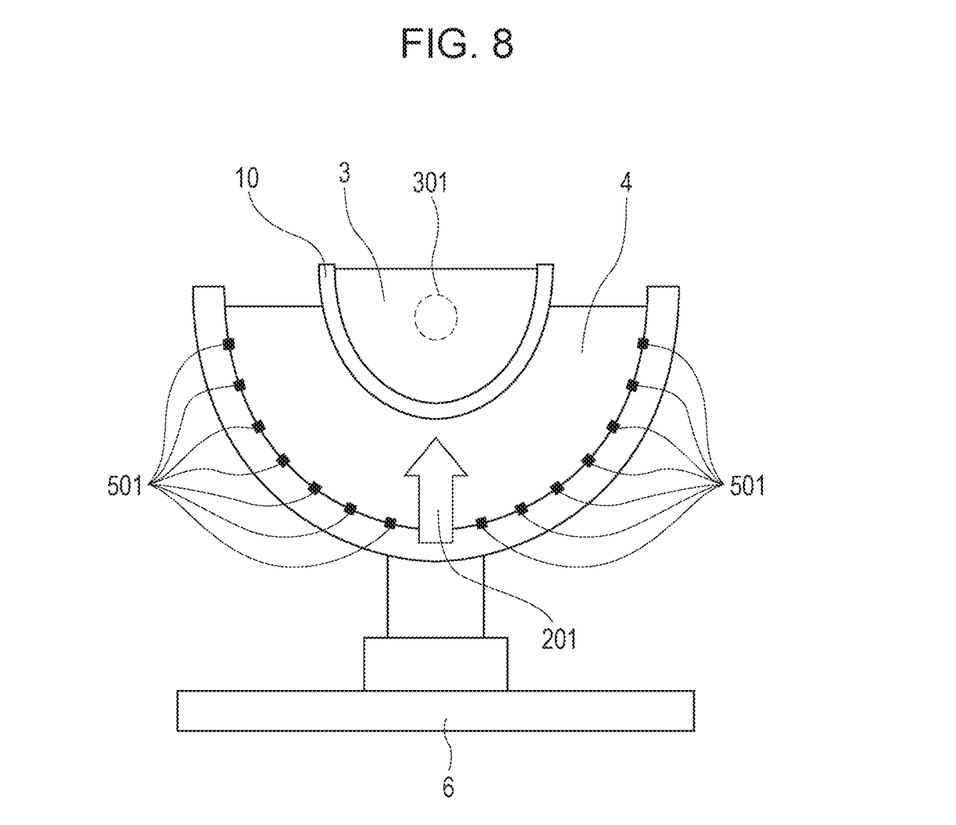
FIG. 8 is a schematic diagram illustrating the apparatus according to the second embodiment of the present invention.

FIG. 7 shows the configuration of an acoustic-wave acquisition apparatus of the second embodiment. The configuration differs from that of the first embodiment in that the subject holder 10 is added as a holding member for holding the subject 3. The second embodiment also differs in a processing method in the data processing unit 8. Since the other configurations are the same as those of the first embodiment, descriptions thereof will be omitted. As shown in FIG. 8, the subject holder 10 holds the subject 3 and defines the shape of the subject 3. The subject holder 10 may be a thin, hard holding member whose acoustic impedance is close to that of the subject 3 or the matching layer 4. More preferably, the acoustic impedance is between those of the subject 3 and the matching layer 4. A specific example is polymethylpentene. Preferably, the subject holder 10 has a thickness of 0.1 mm or more and 5 mm or less.

Figure 4:
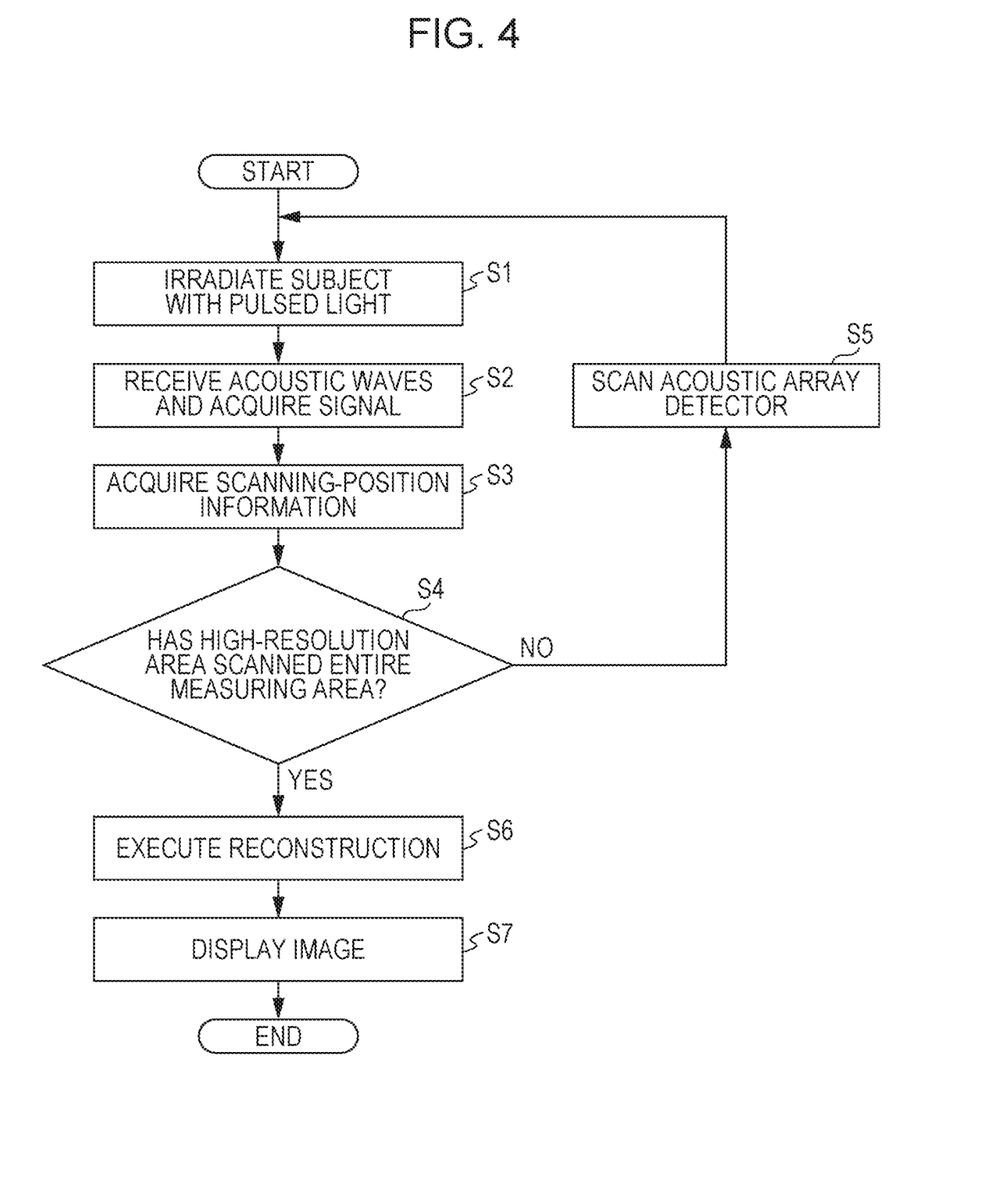
FIG. 4 is a flowchart showing the operation of the apparatus according to the first embodiment of the present invention.

A measuring method of the second embodiment differs from that of the first embodiment in the process of image reconstruction of the data processing unit 8 (S6 in FIG. 4). In this embodiment, the boundary between the subject 3 and the matching layer 4 can be determined from the shape of the subject holder 10, and the area of the subject 3 and the area of the matching layer 4 can be determined from acquired signals by converting distance to time. Here, since the subject holder 10 is sufficiently thin, propagation of acoustic waves in the subject holder 10 is negligible.

Figure 9:
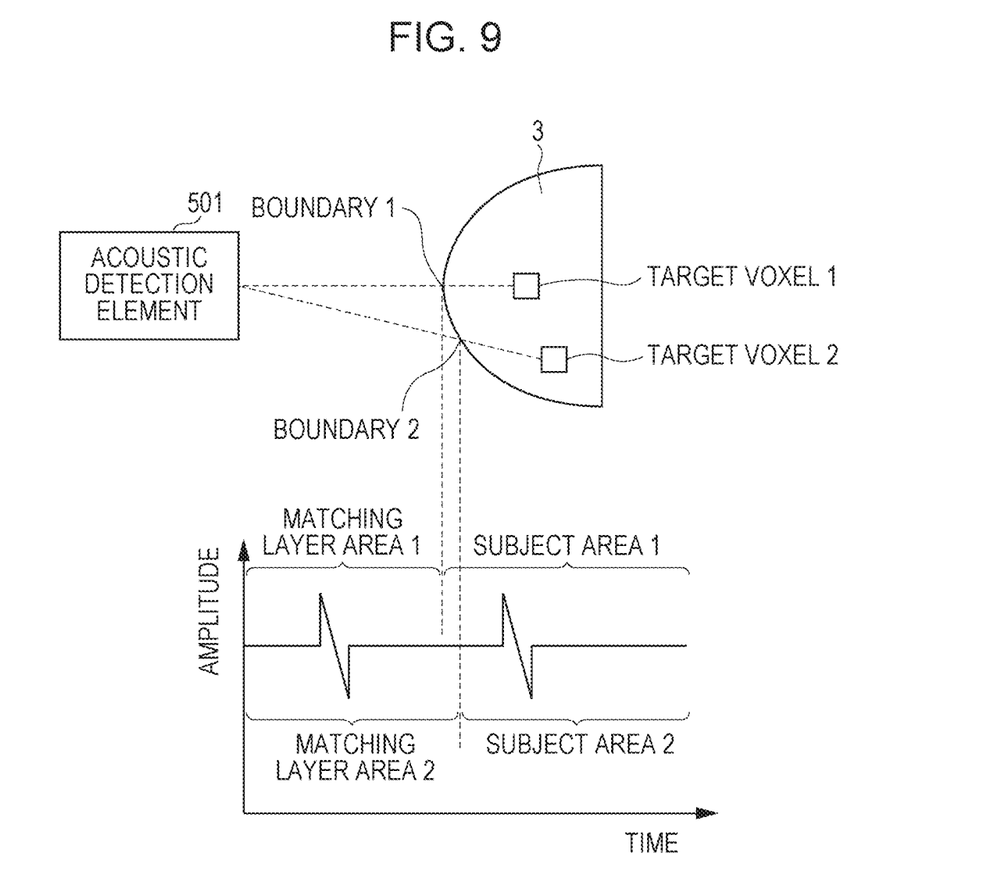
FIG. 9 is a diagram illustrating a processing method of the apparatus according to the second embodiment of the present invention.

For one acoustic detection element 501, the attenuation can generally be properly corrected by dividing signals corresponding to individual areas by acoustic attenuation rates of the individual areas. However, as shown in FIG. 9, a signal obtained by one acoustic detection element 501 is a superimposed signal of signals from a plurality of voxels. The time at the boundary depends on the target voxel, so that the position of the boundary cannot be uniquely determined. Thus, when a target voxel 1 is to be reconstructed, a boundary 1 derived from the positional relationship between the voxel 1 and the acoustic detection element 501 is set, and the signal is divided by an attenuation rate corresponding to the area on the basis of the boundary 1, thereby being corrected. Signals of the other acoustic detection elements 501 are also corrected in the same way, are subjected to pre-processing, such as differentiation, and are superimposed to generate voxel data of the target voxel 1. Also for a target voxel 2, a boundary 2 is set, and correction is performed on the basis of the boundary 2.

With this embodiment, even if different boundaries are set for the same receiver signal, the attenuation can be properly corrected by superimposing the receiver signals of the acoustic detection elements 501. Thus, even if the acoustic attenuation rates of the subject 3 and the matching layer 4 differ, a correct contrast can be calculated.

Figure 10:
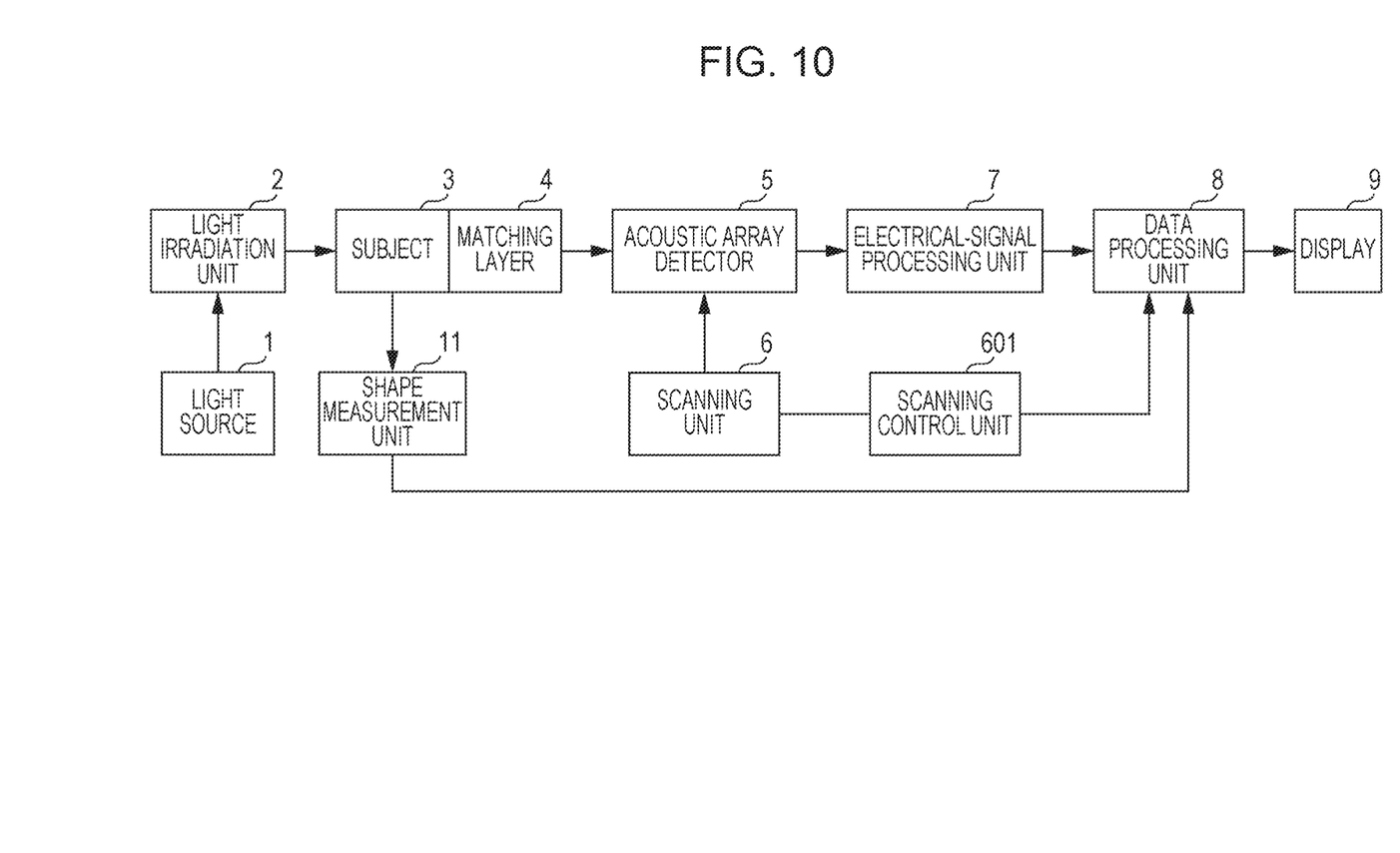
FIG. 10 is a block diagram showing another configuration of the apparatus according to the second embodiment of the present invention.

Furthermore, in this embodiment, the boundary between the subject 3 and the matching layer 4 is determined from the shape of the subject holder 10; instead, as shown in FIG. 10, a method of measuring the outer shape of the subject 3 with a shape measurement unit 11 to obtain the position of the boundary and correcting the contrast is conceivable. With this method, since the subject 3 is not contacted by the subject holder 10, the load on the subject 3 is reduced.

Third Embodiment

[Refraction Correction]

A third embodiment is characterized by correcting signals in consideration of the refraction of acoustic waves at the interface. Although the matching layer 4 may have an acoustic impedance close to that of the subject 3, it is actually difficult to match the impedances completely. Accordingly, since an acoustic impedance is the product of the propagation speed and density of acoustic waves, the propagation speeds of the acoustic waves in the matching layer 4 and the subject 3 sometimes differ. In this case, the acoustic waves are refracted, thus decreasing the resolution. Here, a method for correcting the refraction to improve the resolution will be described.

The configuration of the third embodiment is the same as the configuration of the second embodiment shown in FIG. 7, in which the subject holder 10 is provided as a holding member for holding the subject 3. The third embodiment also differs from the first and second embodiments in a processing method in the data processing unit 8. Since the other configurations are the same as those of the first and second embodiments, descriptions thereof will be omitted.

A measuring method of the second embodiment differs in the process of image reconstruction of the data processing unit 8 (S6 in FIG. 4). In back projection in image reconstruction processing in which pre-processed signals are propagated from the acoustic detection elements 501 in the reverse direction and are superimposed, correction is performed in consideration of refraction caused at the interface between the subject 3 and the matching layer 4 during the back projection. The acoustic velocities of the subject 3 and the matching layer 4 may be measured in advance because they are required to correct the refraction.

As in the second embodiment, the boundary (interface) between the subject 3 and the matching layer 4 can be determined from the shape of the subject holder 10, from which incident angles can be determined. Furthermore, since the acoustic velocities through the subject 3 and the matching layer 4 are known, refractive indexes can be derived from the acoustic velocity ratio. Since the refractive indexes and the angles of incidence are known, refractive angles can be determined from Snell's law. Accordingly, in back projection of the processed signals, the signals are propagated not straight but at the refractive angles calculated at the boundary and are superimposed to generate image data. Also in this embodiment, since the subject holder 10 is sufficiently thin, propagation of acoustic waves in the subject holder 10 is negligible.

With this embodiment, a decrease in resolution due to refraction caused by the difference between acoustic velocities can be corrected. Furthermore, as in the second embodiment, the boundary between the subject 3 and the matching layer 4 can be measured using the shape measurement unit 11 instead of the subject holder 10.

Fourth Embodiment

[Real-Time Display]

Although the reconstruction described in the first embodiment is performed after all the signals have been obtained, measurement results cannot be obtained till the end if the measurement time is long. Furthermore, if the measurement has failed, the time consumed unnecessarily. Thus, in the fourth embodiment, a method for displaying the result in real time will be described.

Although the configuration of the fourth embodiment is the same as that of the first embodiment shown in FIG. 1, processing in the data processing unit 8 differs.

Figure 11:
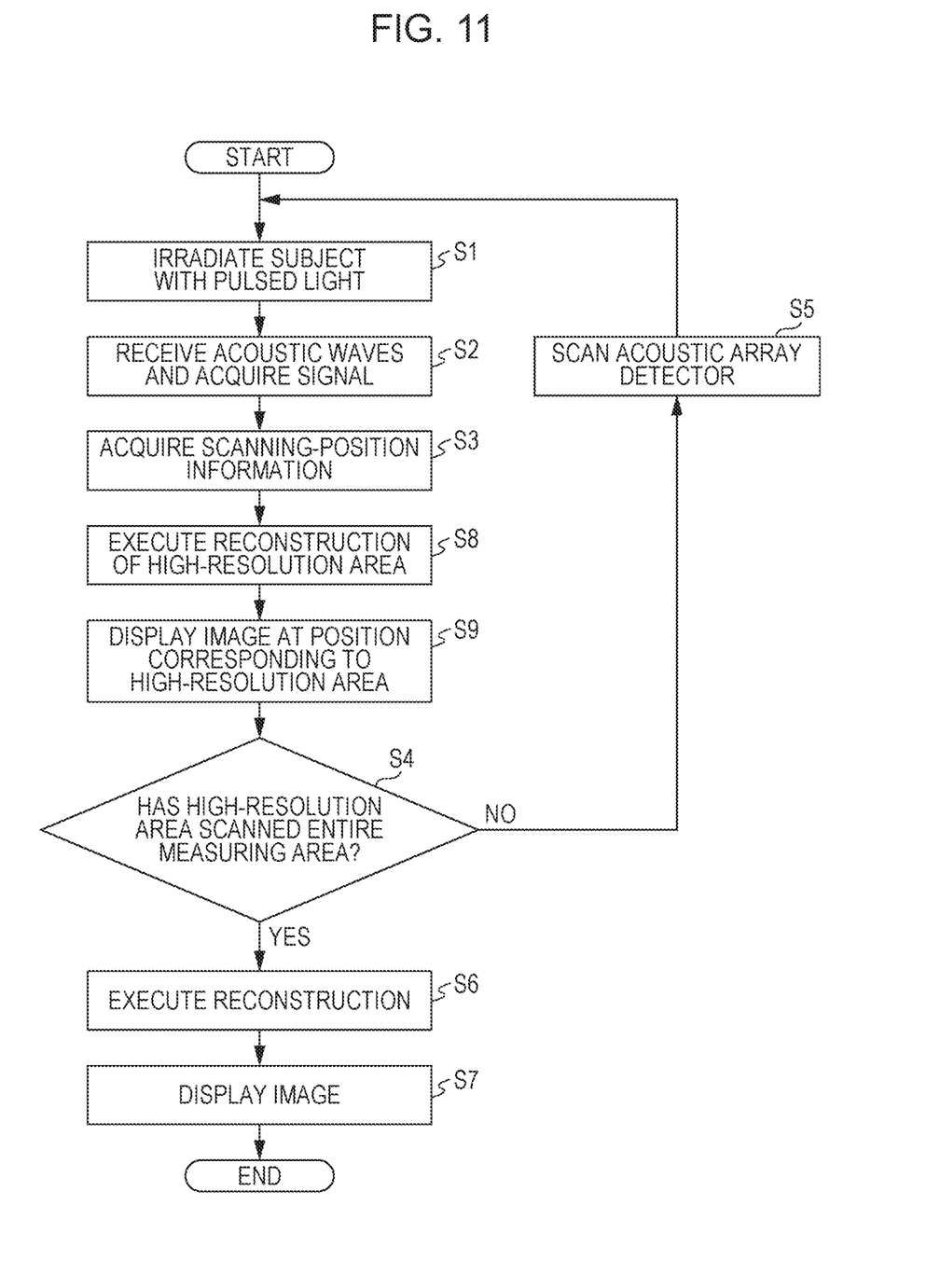
FIG. 11 is a flowchart showing the operation of the apparatus according to a third embodiment of the present invention.

A measuring method of this embodiment will be described with reference to FIG. 11. First, pulsed light is applied to the subject 3 (S1). Acoustic waves excited by the pulsed light are received by the acoustic detection elements 501, are converted to analog receiver signals, and are then converted to digital signals by the electrical-signal processing unit 7 (S2). The data processing unit 8 acquires scanning position information corresponding to the acquired digital signals from the scanning control unit 601 (S3). The data processing unit 8 reconstructs a high-resolution area 301 using the acquired signals (S8). The data processing unit 8 outputs image data reconstructed at a position corresponding to the high-resolution area 301 at that time to the display 9, and the display 9 displays an image (S9).

Next, the scanning control unit 601 determines whether the high-resolution area 301 has finished scanning the entire measuring area (S4). If the scanning has not been finished, the acoustic array detector 5 is scanned (S5). Thereafter, steps S1, S2, S3, S8, and S9 are repeated. Since the scanning step width is smaller than the high-resolution area 301, image display areas at the first measurement and the second measurement are superposed one on another. Thus, image data may be created by determining a mean value for the superposed areas. Repeating the processing allows an image to be displayed in real time. However, since the number of signals for use in reconstruction is small, so that the amount of information is small, the image quality is lower than that of the first embodiment. Accordingly, after completion of scanning, the data processing unit 8 performs reconstruction using all the signals (S6) to overwrite image data and displays it (S7).

The fourth embodiment allows measurement to be performed while the results are being checked in real time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST 1 light source
2 light irradiation unit
3 subject
4 matching layer
5 acoustic array detector
6 scanning unit
7 electrical-signal processing unit
8 data processing unit
9 display
10 subject holder
11 shape measurement unit

The invention claimed is:

1. An acoustic-wave acquisition apparatus comprising;
a detector including a plurality of detection elements including receiving surfaces in a hemispheric arrangement, the detector being configured to receive acoustic waves from a subject;
a shape measurement unit configured to measure an outer shape of the subject; and
a signal processing unit configured to process reception signals from the plurality of detection elements, wherein the signal processing unit changes the reception signal based on measurement results of the shape measurement unit.

2. The acoustic-wave acquisition apparatus according to claim 1, wherein the shape measurement unit detects a boundary between the subject and a matching agent.

3. The information acquisition apparatus according to claim 1, further comprising:
a scanning unit configured to move the detector with respect to the subject.

4. The information acquisition apparatus according to claim 3, further comprising:
a control unit configured to control the movement of the scanning unit.

5. The information acquisition apparatus according to claim 4,
wherein the control unit controls a movement of the detector and a reception of the acoustic waves at predetermined time intervals.

6. The information acquisition apparatus according to claim 3,
wherein the signal processing unit generates a subject information using a plurality of reception signals that are obtained at a plurality of locations of the detector.

7. The information acquisition apparatus according to claim 1, further comprising:
a holding member configured to hold the subject.

8. The information acquisition apparatus according to claim 7,
wherein a diameter of a hemispherical surface formed by the receiving surfaces is at least twice as great as an outside diameter of the holding member.

9. The information acquisition apparatus according to claim 7,
wherein the holding member has a concave portion into which at least a part of the subject is inserted.

10. The information acquisition apparatus according to claim 7,
wherein the holding member has a thickness of 0.1 mm or greater and 5 mm or less.

11. The information acquisition apparatus according to claim 1, further comprising:
a light source configured to generate pulsed light; and
a light irradiation unit optically coupled to the light source and configured to irradiate the subject with the pulsed light,
wherein the acoustic waves are generated at the subject when the subject is irradiated with the pulsed light.

12. The information acquisition apparatus according to claim 11,
wherein the pulsed light has a wavelength from 500 nm to 1,200 nm.

13. The information acquisition apparatus according to claim 11,
wherein the light source is a laser or a light-emitting diode.

14. The information acquisition apparatus according to claim 1, further comprising:
an analog-to-digital (A/D) conversion unit that converts the reception signals outputted by the plurality of detection elements into digital signals.

15. The information acquisition apparatus according to claim 14,
wherein the A/D conversion unit includes a plurality of A/D converters number of which is equal to number of the plurality of detection elements.

16. The information acquisition apparatus according to claim 14,
wherein the A/D conversion unit includes a plurality of A/D converters number of which is less than number of the plurality of detection elements.

17. The information acquisition apparatus according to claim 16,
wherein connection between the plurality of A/D converters and the plurality of detection elements is switched.

18. The information acquisition apparatus according to claim 1,
wherein the signal processing unit performs correction processing on a basis of the information regarding the boundary.

19. The information acquisition apparatus according to claim 18,
wherein the signal processing unit corrects acoustic attenuation rates of the acoustic waves as the correction processing.

20. The information acquisition apparatus according to claim 18,
wherein the signal processing unit performs the correction processing using information regarding acoustic velocities of the subject and an area other than the subject.

* * * * *